(12) United States Patent
Ishida et al.

(10) Patent No.: US 8,592,572 B2
(45) Date of Patent: *Nov. 26, 2013

(54) LIPOSOME CONTAINING SHRNA MOLECULE TARGETING A THYMIDYLATE SYNTHASE AND USE THEREOF

(75) Inventors: Tatsuhiro Ishida, Tokushima (JP); Cheng Long Huang, Kyoto (JP); Hiromi Wada, Otsu (JP)

(73) Assignee: Delta-Fly Pharma, Inc., Tokushima-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/592,002

(22) Filed: Aug. 22, 2012

(65) Prior Publication Data

US 2013/0058996 A1 Mar. 7, 2013

Related U.S. Application Data

(63) Continuation of application No. PCT/JP2012/063082, filed on May 22, 2012, which is a continuation-in-part of application No. 13/273,960, filed on Oct. 14, 2011, now abandoned.

(51) Int. Cl.
 *C07H 21/04* (2006.01)
(52) U.S. Cl.
 USPC ........................................ 536/24.5
(58) Field of Classification Search
 USPC ........................................ 536/24.5
 See application file for complete search history.

(56) References Cited

U.S. PATENT DOCUMENTS

| | | | | |
|---|---|---|---|---|
| 2006/0135456 | A1* | 6/2006 | Hannon et al. | 514/44 |
| 2008/0220027 | A1* | 9/2008 | Liu et al. | 424/400 |
| 2009/0074852 | A1* | 3/2009 | Kaufmann et al. | 424/450 |
| 2009/0318453 | A1* | 12/2009 | Okabe | 514/241 |
| 2010/0130588 | A1* | 5/2010 | Yaworski et al. | 514/44 A |
| 2012/0016012 | A1 | 1/2012 | Wada et al. | |

FOREIGN PATENT DOCUMENTS

| | | |
|---|---|---|
| JP | 2005-253342 A | 9/2005 |
| WO | WO2009/149318 A2 * | 12/2009 |
| WO | WO 2010/113844 A1 | 10/2010 |

OTHER PUBLICATIONS

Tagami et al. Journal of Controlled Release 137, 2009, 234-240.*
Spagnou et al. Biochemistry 2004, 43, 13348-13356.*
International Search Report issued Aug. 21, 2012, in PCT International Application No. PCT/JP2012/063082.
Kim et al., "Enhanced siRNA delivery using cationic liposomes with new polyarginine-conjugated PEG-lipid," International Journal of Pharmaceutics (2010), vol. 392, pp. 141-147.
Uehara et al., "Influence of nucleic-acid-containing PEG-modified nanocarriers on induction of anti-PEG IgM secretion caused by TLR stimulation," The 131st Annual Meeting of the Pharmaceutical Society of Japan, 29P-0464, Feb. 1, 2011, with English translation (http://nenkai.pharm.or.jp/131/pc/imulti_result.asp).
Ishida et al., "Development of siRNA delivery system using a change of intratumoral microenvironment," PH-5014, (The 32nd Symposium on Biomembrane-Drug Interaction, The Pharmaceutical Society of Japan, Division of Physical Sciences, Nov. 29, 2010, pp. 5-8, including an English translation.
Matsunaga et al., "Development of new cancer treatment strategy that combines siRNA-containing liposome with tegaflur formulation S-1," PH-5014 (29P-0463), The 131st Annual Meeting of the Pharmaceutical Society of Japan, Feb. 1, 2011, 6 pages, including an English translation.

* cited by examiner

*Primary Examiner* — Brian Whiteman
(74) *Attorney, Agent, or Firm* — Birch, Stewart, Kolasch & Birch, LLP

(57) ABSTRACT

This method provides a method for delivering shRNA targeting TS in vivo. In addition, the following is provided: an antitumor agent, which comprises short hairpin RNA (shRNA) capable of inhibiting expression of thymidylate synthase by RNAi action and a PEG-modified cationic liposome, wherein the shRNA is bound to the surface of the PEG-modified cationic liposome and has an overhang comprising at least two nucleotides at the 3' end.

17 Claims, 7 Drawing Sheets
(1 of 7 Drawing Sheet(s) Filed in Color)

Fig. 1
(A)
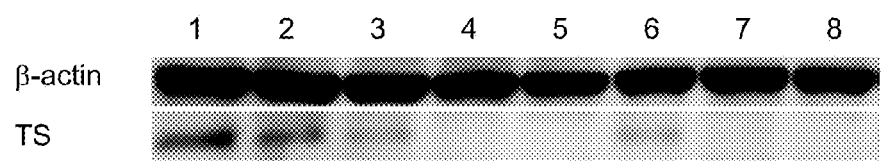
(B)
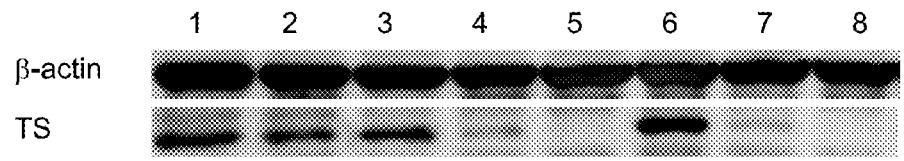

```
                        SEQUENCE LISTING

<160> NUMBER OF SEQ ID NOS: 12

<210> SEQ ID NO 1
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 1
guaacaccau cgaucauga                                                   19

<210> SEQ ID NO 2
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 2
ucaugaucga ugguguuac                                                   19

<210> SEQ ID NO 3
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 3
gaauacagag auauggaau                                                   19

<210> SEQ ID NO 4
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 4
auuccauauc ucuguauuc                                                   19

<210> SEQ ID NO 5
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 5
cgaucaugau guagagugu                                                   19

<210> SEQ ID NO 6
<211> LENGTH: 19
<212> TYPE: RNA
```

```
<213> ORGANISM: Artificial Sequence
<220> FEATURE:
<223> OTHER INFORMATION: synthetic oligonucleotide

<400> SEQUENCE: 6
acacucuaca ucaugaucg                                                    19

<210> SEQ ID NO 7
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 7
uagugcuccu gguug                                                        15

<210> SEQ ID NO 8
<211> LENGTH: 55
<212> TYPE: RNA
<213> ORGANISM: Artificial Sequence
<220> FEATURE:
<223> OTHER INFORMATION: synthetic oligonucleotide

<400> SEQUENCE: 8
guaacaccau cgaucaugau agugcuccug guugucauga ucgauggugu uacuu            55

<210> SEQ ID NO 9
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 9
cuuacgcuga guacuucgat t                                                 21

<210> SEQ ID NO 10
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 10
ucgaaguacu cagcguaagt t                                                 21

<210> SEQ ID NO 11
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 11
ggguguuuug gaggaguugt t                                                 21

<210> SEQ ID NO 12
<211> LENGTH: 21
<212> TYPE: RNA
<213> ORGANISM: Artificial Sequence
<220> FEATURE:
<223> OTHER INFORMATION: synthetic oligonucleotide

<400> SEQUENCE: 12
aacaacuccu ccaaaacacc c                                                 21
```

LIPOSOME CONTAINING SHRNA MOLECULE TARGETING A THYMIDYLATE SYNTHASE AND USE THEREOF

CROSS-REFERENCE TO RELATED APPLICATIONS

This application is a Continuation-in-Part of co-pending U.S. patent application Ser. No. 13/273,960 filed on Oct. 14, 2011, which claims the benefit under 35 U.S.C. 119(a) to Japanese Patent Application No. 2011-114946 filed on May 23, 2011. This application is a Continuation of and also claims priority under 35 U.S.C. 119(a) and 35 U.S.C. 120 to PCT/JP2012/063082 filed on May 22, 2012, which also claims priority to Japanese Patent Application 2011-114946 filed on May 23, 2011. The entire contents of all of the above applications are hereby expressly incorporated by reference in their entirety.

BACKGROUND OF THE INVENTION

1. Field of the Invention

The present invention relates to an antitumor agent comprising, as an active ingredient, a liposome containing a shRNA molecule targeting a thymidylate synthase and the use thereof. In particular, the present invention relates to the use of such antitumor agent in combination with a chemotherapeutic agent.

2. Background Art

In recent years, RNAi molecules that cause RNA interference (hereafter referred to as "RNAi") have been gaining attention as useful tools for treatment of tumors and the like. A variety of RNAi molecules that can inhibit tumor growth have been developed. The present inventors previously reported an RNAi molecule targeting thymidylate synthase (hereafter referred to as "TS") involved in DNA synthesis. In addition, the present inventors reported that the RNAi molecule remarkably inhibits TS expression and thus exhibits the antitumor effects, and that the RNAi molecule potentiates the antitumor effects of a 5-FU antitumor agent (and particularly a compound drug of tegafur, gimeracil, and oteracil potassium) (WO2010/113844).

However, in general, RNAi molecules quickly disintegrate upon in vivo administration. Therefore, it has been very difficult to deliver RNAi molecules at sufficient amounts for targeting tumors.

In order to solve the above problems, a variety of RNAi molecule delivery methods are currently under development. For example, there is a method comprising incorporating DNA encoding an RNAi molecule (and particularly an RNAi molecule having a short hairpin structure (shRNA)) into an adequate vector and administering the vector (WO2010/113844). However, according to this method, it is necessary to directly inject the vector into a tumor for administration. In view of clinical application, an easier administration method (e.g., intravenous administration) has been awaited. In addition, methods for delivering RNAi molecules to tumor cells using complexes (lipoplexes) prepared by mixing an RNAi molecule with a liposome have been developed (Qixin Leng et al., Drug Future, 2009 September, 34(9), 721; Sherry Y. Wu et al., The AAPS Journal, Vol. 11, No. 4, December 2009; and B. Ozpolat et al., Journal of Internal Medicine 267; 44-53 2009). However, upon repetitive administration of such lipoplexes, the lipoplexes are quickly trapped by the cells of immune systems of living bodies to which the lipoplexes have been administered. In such case, sufficient RNAi effects cannot be obtained. In addition, such administration can cause serious side effects, which is problematic.

Therefore, a method for efficiently delivering RNAi molecules to tumors via in vivo administration still has been awaited in the art.

SUMMARY OF THE INVENTION

An object of the present invention is to provide a method for convenient and efficient in vivo delivery of shRNA targeting TS.

As a result of intensive studies in order to solve the above problems, the present inventors found that when shRNA capable of inhibiting TS expression is electrostatically bound to the surface of a PEG-modified cationic liposome, the shRNA bound to the liposome can be readily delivered to cancer cells. In addition, the present inventors found that when a PEG-modified cationic liposome to which shRNA has been bound is used in combination with a chemotherapeutic agent, and particularly, a 5-FU antitumor agent, cancer cell targetability can be enhanced, thereby allowing remarkably improving effects against cancer cells. Further, the present inventors found that when a PEG-modified cationic liposome to which shRNA has been bound is used in combination with a chemotherapeutic agent having TS inhibitory action (e.g., a 5-FU antitumor agent or a pemetrexed sodium hydrate), sensitivity of cancer cells against the chemotherapeutic agent can be enhanced, thereby potentiating the antitumor effects. The present invention has been made based on the above findings.

Specifically, the present invention is described as follows.
[1] An antitumor agent, which comprises short hairpin RNA (shRNA) capable of inhibiting expression of thymidylate synthase by RNAi action and a PEG-modified cationic liposome, wherein the shRNA is bound to the surface of the PEG-modified cationic liposome and has an overhang comprising at least two nucleotides at the 3' end.
[2] The antitumor agent according to [1], wherein the shRNA comprises a sense strand consisting of the nucleotide sequence shown in SEQ ID NO: 1 and an antisense strand that hybridizes under stringent conditions to the sense strand.
[3] The antitumor agent according to [1] or [2], wherein the shRNA comprises a sense strand consisting of the nucleotide sequence shown in SEQ ID NO: 1 and an antisense strand consisting of the nucleotide sequence shown in SEQ ID NO: 2.
[4] The antitumor agent according to any one of [1] to [3], wherein the shRNA consists of the nucleotide sequence shown in SEQ ID NO: 8.
[5] The antitumor agent according to any one of [1] to [4], wherein the PEG-modified cationic liposome comprises a cationic liposome composed of dioleoylphosphatidylethanolamine (DOPE), palmitoyloleoylglycerophosphocholine (POPC), cholesterol (CHOL), and O,O'-ditetradecanoyl-N-(α-trimethylammonioacetyl)diethanolaminechloride (DC-6-14).
[6] The antitumor agent according to [5], which contains DOPE, POPC, CHOL, and DC-6-14 at a molar ratio of 3:2:3:2.
[7] The antitumor agent according to any one of [1] to [6], wherein the particle size of the antitumor agent is 200 to 300 nm.
[8] The antitumor agent according to any one of [1] to [7], wherein further siRNA or shRNA capable of inhibiting expression of a gene selected from the group consisting of genes involved in tumor cell proliferation is bound to the surface of the PEG-modified cationic liposome.

[9] The antitumor agent according to [8], wherein the gene involved in tumor cell proliferation is at least one gene selected from the group consisting of genes encoding VEGF, EGFR, PDGF, HGF, Wint, Bcl-2, survivin, ribonucleotide reductase, and DNA polymerase.
[10] The antitumor agent according to any one of [1] to [9], which is used in combination with a chemotherapeutic agent for treating tumors.
[11] A combined product, which contains the antitumor agent according to any one of [1] to [10] and a chemotherapeutic agent for treating tumors.
[12] The antitumor agent according to [10] or the combined product according to [11], wherein the chemotherapeutic agent for treating tumors is an antitumor agent having TS inhibitory action.
[13] The antitumor agent or the combined product according to [12], wherein the antitumor agent having TS inhibitory action is a 5-FU antitumor agent or a pemetrexed sodium hydrate.
[14] The antitumor agent or the combined product according to [13], wherein the 5-FU antitumor agent is a compound drug of tegafur, gimeracil, and oteracil potassium.
[15] A method for treating cancer, which comprises administering the antitumor agent according to any one of [1] to [9] to a cancer patient.
[16] The method according to [15], which further comprises administrating a chemotherapeutic agent for treating tumors in combination with the antitumor agent.
[17] The method according to [16], wherein the chemotherapeutic agent for treating tumors is an antitumor agent having TS inhibitory action.
[18] The method according to [17], wherein the antitumor agent having TS inhibitory action is a 5-FU antitumor agent or a pemetrexed sodium hydrate.
[19] The method according to [18], wherein the 5-FU antitumor agent is a compound drug of tegafur, gimeracil, and oteracil potassium.
[20] The method according to any one of [15] to [19], wherein the cancer is selected from the group consisting of colorectal cancer, liver cancer, kidney cancer, head and neck cancer, esophageal cancer, gastric cancer, biliary tract cancer, gallbladder and bile duct cancer, pancreatic cancer, lung cancer, mammary cancer, ovarian cancer, cervical cancer, uterine body cancer, bladder cancer, prostate cancer, testicular tumor, osteogenic and soft-tissue sarcomas, leukaemia, malignant lymphoma, multiple myeloma, skin cancer, brain tumor and plura malignant mesothelioma.

This description includes part or all of the contents as disclosed in the description and/or drawings of Japanese Patent Application No. 2011-114946, which is a priority document of the present application.

The antitumor agent comprising, as an active ingredient, a liposome containing a shRNA molecule targeting a thymidylate synthase of the present invention can inhibit growth of TS-expressing tumors via in vivo administration.

BRIEF DESCRIPTION OF THE DRAWINGS

The patent or application file contains at least one color drawing. Copies of this patent or patent application publication with color drawing will be provided by the USPTO upon request and payment of the necessary fee.

FIG. 1 shows a characteristic image indicating TS expression inhibitory effects of siRNA and shRNA targeting TS for human colorectal cancer cell lines (DLD-1(A) and DLD-1/FU(B)). Each lane shows the results for the following samples treated with siRNA or shRNA: 1: Untreated; 2: 10 nM siCont; 3: 1 nM siTS; 4: 5 nM siTS; 5: 10 nM siTS; 6: 1 nM shTS; 7: 5 nM shTS; and 8: 10 nM shTS.

FIGS. 2(A) and 2(B) each show a characteristic chart indicating TS expression inhibitory effects on cell growth for (A): siRNA targeting TS; and (B): shRNA targeting TS confirmed in a human colorectal cancer cell line (DLD-1) under the presence or absence of 5-FU.

FIGS. 3(A) and 3(B) each show a characteristic chart indicating TS expression inhibitory effects on cell growth for (A): siRNA targeting TS; and (B): shRNA targeting TS confirmed in a human colorectal cancer cell line (DLD-1/FU) under the presence or absence of 5-FU.

DESCRIPTION OF THE PREFERRED EMBODIMENTS

Figure 2:
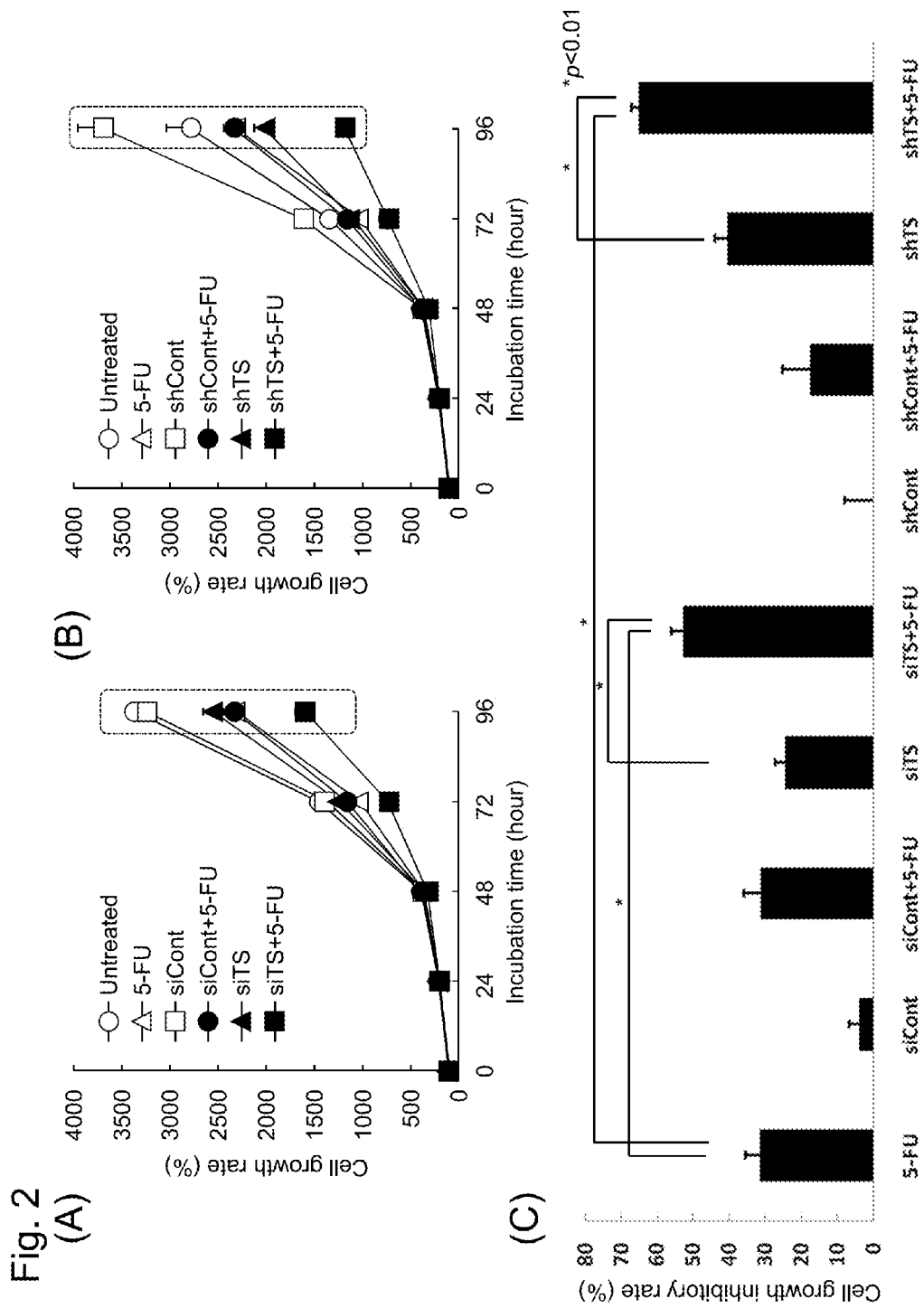
FIG. 2 (C) shows the cell growth inhibitory rate (%) for each sample 96 hours after the addition of fresh medium.

The short hairpin RNA (hereafter referred to as "shRNA") capable of inhibiting expression of thymidylate synthase (hereafter referred to as "TS") of the present invention exhibits TS-specific RNAi action when it targets an mRNA portion of thymidylate synthase. Accordingly, the short hairpin RNA can remarkably inhibit TS expression. Here, when the RNAi molecule of the present invention "targets an mRNA portion," this means that the antisense strand of shRNA described in detail below can hybridize to a target mRNA portion under stringent conditions.

Stringent conditions can be determined based on the melting temperature (Tm) for nucleic acid at which a hybrid is formed in accordance with a conventional method. For instance, washing conditions that allows maintenance of hybridization comprise, for example, generally "1×SSC, 0.1% SDS, 37° C.," more strictly "0.5×SSC, 0.1% SDS, 42° C.," and further strictly "0.1×SSC, 0.1% SDS, 65° C."

The shRNA of the present invention comprises a sense strand having a nucleotide sequence of ORF encoding TS or a nucleotide sequence partially identical thereto and an antisense strand that hybridizes under stringent conditions to the sense strand. Here, the phrase "a nucleotide sequence of ORF or a nucleotide sequence partially identical thereto" means a nucleotide sequence obtained by substituting thymine with uracil in the nucleotide sequence of ORF or a nucleotide sequence partially identical thereto.

The sense strand consists of 15 to 25 nucleotides and preferably 19 nucleotides. The nucleotide sequence of the sense strand is desirably identical to the nucleotide sequence of ORF encoding TS. However, it may be a substantially identical (i.e., homologous) sequence. Specifically, the nucleotide sequence of a sense strand may comprise the ORF nucleotide sequence including a substitution, a deletion, an insertion, and/or an addition of 1 or a plurality of (i.e., 1 to 3) nucleotides, preferably 1 to 2 nucleotides, and more preferably 1 nucleotide.

The antisense strand has a nucleotide sequence that can hybridize to the sense strand under stringent conditions. The antisense strand may comprise a mismatch, including a substitution, a deletion, an insertion, and/or an addition of 1 to 3 nucleotides, preferably 1 or 2 nucleotides, and more preferably 1 nucleotide as long as it can hybridize under stringent conditions. Preferably, the antisense strand consists of a nucleotide sequence perfectly complementary to the sense strand.

The nucleotide sequences of a sense strand and an antisense strand can be selected based on a known nucleotide sequence encoding TS (GenBank: CR601528.1). There are a variety of known methods for selecting such nucleotide sequences. For example, an siRNA Design Support System (Takara Bio Inc.) can be used.

Examples of a sense strand used in the present invention include, but are not limited to, a sense strand consisting of any of the following nucleotide sequences: 5'-GUAACAC-CAUCGAUCAUGA-3' (SEQ ID NO: 1); 5'-GAAUACA-GAGAUAUGGAAU-3' (SEQ ID NO: 3); 5'-CGAUCAUGAUGUAGAGUGU-3' (SEQ ID NO: 5); and 5'-GGGUGUUUUGGAGGAGUUGTT-3' (SEQ ID NO: 11).

Preferably, shRNA of the present invention comprises: a sense strand (5'-GUAACACCAUCGAUCAUGA-3'; SEQ ID NO: 1) and an antisense strand (5'-UCAUGAUCGAUGGU-GUUAC-3'; SEQ ID NO: 2); a sense strand (5'-GAAUACA-GAGAUAUGGAAU-3'; SEQ ID NO: 3) and an antisense strand (5'-AUUCCAUAUCUCUGUAUUC; SEQ ID NO: 4); a sense strand (5'-CGAUCAUGAUGUAGAGUGU-3'; SEQ ID NO: 5) and an antisense strand (5'-ACACUCUACAU-CAUGAUCG-3'; SEQ ID NO: 6); or a sense strand (5'-GGGUGUUUUGGAGGAGUUGTT-3'; SEQ ID NO: 11) and an antisense strand (5'-AACAACUCCUCCAAAA-CACCC-3'; SEQ ID NO: 12).

Further preferably, shRNA of the present invention comprises a sense strand consisting of the nucleotide sequence shown in SEQ ID NO: 1 and an antisense strand consisting of the nucleotide sequence shown in SEQ ID NO: 2.

A sense strand and an antisense strand are linked via a linker portion. The linker portion forms a loop such that the resulting strand is folded. Accordingly, the antisense strand and the sense strand hybridize to each other, resulting in formation of a double strand. Such a linker portion contained in a shRNA molecule is not particularly limited and thus it may be a polynucleotide linker or a non-polynucleotide linker as long as it links a sense strand and an antisense strand so as to form a stem loop structure. Preferably, a polynucleotide linker is the same consisting of 2 to 22 nucleotides known in the art. Specific examples thereof include UAGUGCUC-CUGGUUG (SEQ ID NO: 7), UUCAAGAGA, CCACC, CUCGAG, CCACACC, UUCAAGAGA, AUG, CCC, and UUCG. Of these, UAGUGCUCCUGGUUG (SEQ ID NO: 7) is preferable.

shRNA of the present invention has an overhang comprising at least 2 nucleotides at the 3' end.

According to the present invention, the term "overhang" refers to a nucleotide added at the 3' end of an antisense strand that does not have a nucleotide capable of complementarily binding at a position corresponding to a sense strand. If an antisense strand does not have an overhang at the 3' end, the degree of TS expression inhibition caused by shRNA decreases by approximately 40% to 60% upon transfection with the use of a PEG-modified cationic liposome described in detail below, compared with a case in which an antisense strand has an overhang at the 3' end. Types or numbers of nucleotides of the overhang are not limited. For example, such overhang consists of a sequence comprising 1 to 5 nucleotides, preferably 1 to 3 nucleotides, and more preferably 1 or 2 nucleotides. Examples of a sequence include TTT, UU, and TT. Preferably, UU is used.

According to the present invention, a preferable example of shRNA is a single strand RNA consisting of the nucleotide sequence shown in SEQ ID NO: 8.

In addition, a sense strand or an antisense strand may be phosphorylated at the 5' end according to need. Triphosphoric acid (ppp) may be bound to the 5' end.

In the case of the PEG-modified cationic liposome of the present invention, one or a plurality of polyethyleneglycol (PEG) molecules are covalently bound to the cationic liposome surface, allowing the cationic liposome to have improved ability to circulate in vivo.

The cationic liposome can be produced by a known method, such as a thin film shaking method (the Bangham method) (A. D. Bangham et al., J. Mol. Biol., 13, 238-252 (1965); A. D. Bangham and R. W. Horne, J. Mol. Biol., 8, 660-668 (1964)). Specifically, at least one type of phospholipid is dissolved in an organic solvent such as chloroform in a container such as a flask. The organic solvent is evaporated to form a lipid membrane on the bottom of the container. An aqueous solution such as buffer is introduced thereinto, followed by agitation. Thus, a suspension containing liposomes can be obtained.

The cationic liposome of the present invention has uni- or multi-lamellar membranes consisting of at least one phospholipid selected from the group consisting of dioleoylphosphatidylethanolamine (hereafter referred to as "DOPE"), palmitoyloleoylglycerophosphocholine (hereafter referred to as "POPC"), cholesterol (hereafter referred to as "CHOL"), O,O'-ditetradecanoyl-N-(α-trimethylammonioacetyl)diethanolaminechloride (hereafter referred to as "DC-6-14"), hydrogenated purified yolk phosphatidylcholine, hydrogenated purified soybean phosphatidylcholine, dipalmitoyl phosphatidylcholine, distearoyl phosphatidylcholine, and 1-palmitoyl-2-oleoyl phosphatidylcholine.

Preferably, the cationic liposome of the present invention consists of DOPE, POPC, CHOL, and DC-6-14. The content ratio (molar ratio) of DOPE, POPC, CHOL, and DC-6-14 in the cationic liposome is DOPE:POPC:CHOL:DC-6-14=2 to 4:4 to 1:3 to 1:1 to 4 and preferably 3:2:3:2.

A PEG molecule bound to the cationic liposome surface is selected from PEG molecules having molecular weights of 500 to 5000 and preferably approximately 2000. Binding of PEG to a cationic liposome can be carried out by a known method which is not particularly limited. However, a post insertion method or the like can be used. Specifically, after formation of the cationic liposome, a PEGylated phospholipid is incubated with the cationic liposome under appropriate conditions (e.g., 30° C. to 60° C. for 30 minutes to 3 hours). Thus, the lipid portion of the PEGylated phospholipid can be incorporated into the outer phospholipid membrane of the cationic liposome in a manner such that PEG is exposed on the cationic liposome surface. At such time, the amount of the PEGylated phospholipid used for the incorporation accounts for 3% to 10% and preferably 5% (molar percentage) of the total lipid amount of the cationic liposome. Examples of the PEGylated phospholipid that can be used according to the present invention include, but are not limited to, mPEG$_{2000}$-DSPE.

The PEG-modified cationic liposome of the present invention has a particle size of 80 to 200 nm and preferably approximately 100 nm. The PEG-modified cationic liposome of the present invention has a zeta potential of 10 to 40 mV and preferably approximately 25 mV.

The above shRNA is covalently or noncovalently bound to the membrane surface of the PEG-modified cationic liposome. In order to bind the shRNA to the PEG-modified cationic liposome, it is desirable to intensively agitate a liquid mixture containing the shRNA and the PEG-modified cationic liposome for approximately 1 to 15 minutes and preferably 10 minutes. Agitation allows adjustment of the particle size of a PEG-modified cationic liposome containing shRNA that can be obtained to several hundred nanometers (Barichello, J. M., et al., Int. J. Pharm. 410, 153-160 (2011)). In addition, agitation allows uniform dispersion of the shRNA on the surface of PEG-modified cationic liposome at binding. Therefore, it is possible to prevent irregular tissue distribution of the PEG-modified cationic liposome due to nonuniform binding of shRNA on the liposome.

According to the present invention, the PEG-modified cationic liposome containing shRNA has a particle size of 120 to 600 nm and preferably 200 to 300 nm. In addition, the PEG-modified cationic liposome containing shRNA has a zeta potential of 5 to 30 mV and preferably approximately 10 to 25 mV according to the present invention. The surface charge of the PEG-modified cationic liposome containing shRNA is close to neutral. In addition, the PEG-modified cationic liposome containing shRNA is unlikely to bind to a serum protein due to PEG-induced steric hindrance. Therefore, the liposome can be prevented from being trapped in lung alveoli, allowing the liposome to have improved ability to circulate in vivo.

The PEG-modified cationic liposome containing shRNA of the present invention may contain further shRNA or siRNA targeting a different gene expressed in tumor cells, in addition to the above shRNA. Examples of "a different gene expressed in tumor cells" include, but are not limited to, genes encoding factors involved in tumor cell proliferation, for example, the growth regulatory factor group (consisting of VEGF, EGFR, PDGF, HGF, Wint, Bcl-2, survivin, and the like) and the nucleotide synthesis-related enzyme group (consisting of ribonucleotide reductase, DNA polymerase, and the like). The above shRNA and the siRNA or sh RNA targeting a different gene expressed in tumor cells may be bound to an identical PEG-modified cationic liposome or they may be separately bound to different PEG-modified cationic liposomes.

Here, the PEG-modified cationic liposome containing shRNA is sometimes referred to as "PEG-modified lipoplex."

As described detail in the Examples below, it is possible for the PEG-modified cationic liposome containing shRNA to inhibit tumor cell proliferation as a result of in vivo administration. Therefore, it can be used as an antitumor agent for treating cancer.

Cancers exhibiting high TS expression levels can be treated with the antitumor agent of the present invention. Examples of such cancers include, but are not particularly limited to, colorectal cancer, liver cancer, kidney cancer, head and neck cancer, esophageal cancer, gastric cancer, biliary tract cancer, gallbladder and bile duct cancer, pancreatic cancer, lung cancer, mammary cancer, ovarian cancer, cervical cancer, uterine body cancer, bladder cancer, prostate cancer, testicular tumor, osteogenic and soft-tissue sarcomas, leukaemia, malignant lymphoma, multiple myeloma, skin cancer, brain tumor and plura malignant mesothelioma. Preferable examples are colorectal cancer, gastric cancer, head and neck cancer, lung cancer, mammary cancer, pancreatic cancer, biliary tract cancer, liver cancer and plura malignant mesothelioma. Of these, colorectal cancer and plura malignant mesothelioma are particularly preferable.

The antitumor agent of the present invention may contain additives that can be used for production of medicines, in addition to the PEG-modified cationic liposome containing shRNA. Examples of such additives include excipients, binders, disintegrators, lubricants, diluents, solubilizers, suspending agents, isotonizing agents, pH modifiers, buffers, stabilizers, colorants, flavoring agents, corrigents, and histidine.

Examples of excipients include lactose, sucrose, sodium chloride, glucose, maltose, mannitol, erythritol, xylitol, maltitol, inositol, dextran, sorbitol, albumin, urea, starch, calcium carbonate, kaoline, crystalline cellulose, silica, methylcellulose, glycerine, sodium alginate, gum Arabic, and a mixture of any thereof. Examples of lubricants include purified talc, stearate, sodium borate, polyethylene glycol, and a mixture of any thereof. Examples of binders include simple syrup, glucose solution, starch solution, gelatin solution, polyvinyl alcohol, polyvinyl ether, polyvinyl pyrrolidone, carboxymethyl cellulose, shellac, methylcellulose, ethyl cellulose, water, ethanol, potassium phosphate, and a mixture of any thereof. Examples of disintegrators include dry starch, sodium alginate, agar powder, laminaran powder, sodium bicarbonate, calcium carbonate, polyoxyethylene sorbitan fatty acid esters, sodium lauryl sulfate, stearic acid monoglyceride, starch, lactose, and a mixture of any thereof. Examples of diluents include water, ethyl alcohol, macrogol, propylene glycol, ethoxylated isostearyl alcohol, polyoxylated isostearyl alcohol, polyoxyethylene sorbitan fatty acid esters, and a mixture of any thereof. Examples of stabilizers include sodium pyrosulfife, ethylenediaminetetraacetic acid, thioglycolic acid, thiolactic acid, and a mixture of any thereof. Examples of isotonizing agents include sodium chloride, boric acid, glucose, glycerine, and a mixture of any thereof. Examples of pH modifiers and buffers include sodium citrate, citric acid, sodium acetate, sodium phosphate, and a mixture of any thereof.

The antitumor agent of the present invention can be administered through an oral or parenteral route (e.g., intravenous administration, intraarterial administration, topical administration via injection, intraperitoneal or intrathoracic administration, subcutaneous administration, intramuscular administration, sublingual administration, percutaneous absorption, or intrarectal administration). Preferably, the antitumor agent of the present invention can be administered via intravenous administration, intraperitoneal administration, or intrathoracic administration.

The antitumor agent of the present invention can be prepared in an adequate dosage form in accordance with the route of administration. Specifically, the antitumor agent can be prepared in various dosage forms, such as injection preparations, suspensions, emulsifiers, ointments, creams, tablets, capsules, granule preparations, powder preparations, pills, fine grains, troches, drug preparations for intrarectal administration, oleagenous suppositories, or water-soluble suppositories.

Effects of the antitumor agent of the present invention can be evaluated by administering the antitumor agent to cells or tissues from the above cancer or individuals who have contracted the cancer, comparing the tumor sizes with the cellular or tissue tumor sizes from the above cancer or individuals who have contracted the cancer to which the antitumor agent has not been administered (or prior to administration), and confirming whether or not tumor shrinkage or disappearance can be observed. Cancer cells used for evaluation of effects of the antitumor agent of the present invention are not limited to a particular type of cancer cells, as long as TS is expressed in the cells. Examples of cancer cells used for evaluation of effects of the antitumor agent of the present invention include: human colorectal cancer cell lines such as DLD-1, DLD-1/5FU (a 5-FU-resistant DLD-1 cell line), KM12C/5FU (a 5-FU-resistant KM12C cell line), and HT29/5FU (a 5-FU-resistant HT29 cell line); and a human gastric cancer cell line such as NUGC-3/5FU (a 5-FU-resistant NUGC-3 cell line); and a human mesothelioma cell line (METO 211 H).

The antitumor agent of the present invention is capable of exerting antitumor effects that are two, three, four, five, ten, twenty, thirty, forty, fifty, one hundred, or more times as great as an antitumor agent comprising RNAi molecule targeting TS mRNA as an active ingredient, which is known in the art.

A viral vector containing DNA encoding shRNA has been conventionally used for in vivo delivery of shRNA to target cells (WO2010/113844). The DNA encoding shRNA is transferred into cells by making use of water pressure upon injection of the viral vector or viral infection, resulting in intranuclear expression of shRNA. As in the case of endogenous shRNA, the expressed shRNA comes into contact with an enzyme called "dicer" such that the stem loop construct is cleaved therefrom. Thus, siRNA consisting of a double strand RNA (consisting of strands complementary to each other) is formed such that RNAi action is exhibited. Meanwhile, as a result of oral or parenteral administration of the antitumor agent of the present invention, shRNA complexed with a PEG-modified cationic liposome in the agent is delivered to tumor cells. shRNA delivered to tumor cells is transferred to the insides of cells via endocytosis. Specifically, unlike the above conventional technique, shRNA of the present invention is not shRNA expressed in target cells. The present inventors found for the first time that exogenous shRNA introduced extracellularly in vivo can exhibit RNAi action without being degraded and thus it can inhibit expression of an endogenous gene expressed in target cells.

In addition, if siRNA is coupled to a PEG-modified cationic liposome, it would be probable that a sense strand or antisense strand alone of siRNA that does not form a double strand (consisting of strands complementary to each other) would bind to the PEG-modified cationic liposome during the manufacturing process. Such PEG-modified cationic liposome containing only a sense strand or antisense strand of siRNA can be regarded as an impurity and therefore such liposome is an undesirable pharmacological product. Meanwhile, in the case of PEG-modified cationic liposome containing shRNA, such impurity is unlikely to be formed and thus the liposome can be a desirable pharmacological product.

The antitumor agent of the present invention can be used with an existing chemotherapeutic agent. Examples of an existing chemotherapeutic agent include an antitumor agent having TS inhibitory action.

Such "antitumor agent having TS inhibitory action" is not particularly limited as long as it can inhibit the function of TS. Examples thereof include 5-FU antitumor agents, pemetrexed sodium hydrate, raltitrexed (Tomudex), methotrexate (MTX), and OSI-7904L (OSI).

The relationship between the TS expression level and the sensitivity of a 5-FU antitumor agent has been reported (Patrick G. Johnston et al., Cancer Res 1995; 55: 1407-12 and Kun-Huei Yeh et al., Cancer 1998; 82: 1626-31). Among cancer patients, 5-FU antitumor agents are remarkably effective for cancer patients with relatively low TS expression levels, while on the other hand, cancer patients with relatively high TS expression levels have resistance to 5-FU antitumor agents. Administration of the antitumor agent of the present invention enables suppression of TS production in tumor tissue, allowing an increase in the sensitivity of a 5-FU antitumor agent in such tumor tissue. In addition, the PEG-modified cationic liposome is selectively accumulated in tumors when used in combination with a 5-FU antitumor agent (Yusuke Doi et al., Cancer Sci, November, 2010, vol. 101, no. 11, 2470-2475).

When the antitumor agent of the present invention containing the PEG-modified cationic liposome is used in combination with a 5-FU antitumor agent, the agent has the above effects and thus shRNA can be delivered to tumors with good efficiency. The antitumor agent of the present invention is capable of exerting antitumor effects that are two, three, four, five, or more times as great as a 5-FU antitumor agent or the antitumor agent of the present invention used alone.

Examples of 5-FU antitumor agents include 5-FU and a 5-FU derivative from which 5-FU is produced as an active metabolite. An example of a 5-FU derivative is an agent containing tegafur. A 5-FU derivative is preferably a compound drug containing tegafur. Specific examples thereof include a compound drug of tegafur and uracil (e.g., UFT (registered trademark) (Taiho Phamaceutical Co., Ltd.)), a compound drug of tegafur, gimeracil, and oteracil potassium. The compound drug of tegafur, gimeracil, and oteracil potassium (e.g., TS-1 (registered trademark), Taiho Phamaceutical Co., Ltd.) described below is particularly preferable. In addition, 5-FU antitumor agent is herein referred to as "5-1," or "TS-1." However, such terms can be interchangeably used.

In addition, an example of pemetrexed sodium hydrate is Alimta (registered trademark) (Eli Lilly Japan K.K.). Also, as in the case of the 5-FU antitumor agent, shRNA can be efficiently delivered to tumors when pemetrexed sodium hydrate and the antitumor agent of the present invention are used in combination. Furthermore, a combination use of pemetrexed sodium hydrate and the antitumor agent of the present invention results in remarkably significant antitumor effects that are two, three, four, five, or more times as great as the those of pemetrexed sodium hydrate or the antitumor agent of the present invention used alone.

The antitumor agent of the present invention can be used in combination with a different existing chemotherapeutic agent in addition to or instead of the antitumor agent having TS inhibitory action. Examples of such chemotherapeutic agent include cyclophosphamide, nitrogen mustard N-oxide, ifosfamide, melphalan, busulphan, mitobronitol, carboquone, thiotepa, ranimustine, nimustine, temozolomide, carmustine, pemetrexed disodium, methotrexate, 6-mercaptopurine riboside, mercaptopurine, doxifluridine, carmofur, cytarabine, cytarabine ocfosfate, enocitabine, gemcitabine, fludarabine, pemetrexed, cisplatin, carboplatin, oxaliplatin, paclitaxel, docetaxel, irinotecan hydrochloride, and capecitabine. One or a plurality of chemotherapeutic agents selected from the examples can be used. Also, as in the case of the antitumor agent having TS inhibitory action, shRNA can be efficiently delivered to tumors when the above chemotherapeutic agent and the antitumor agent of the present invention are used in combination. Furthermore, the combination use of the chemotherapeutic agent and the antitumor agent of the present invention results in remarkably significant antitumor effects two, three, four, five, or more times as great as the chemotherapeutic agent or the antitumor agent of the present invention used alone.

A combined product of the antitumor agent of the present invention and an existing chemotherapeutic agent can be provided as long as the antitumor agent of the present invention and the existing chemotherapeutic agent are administered in combination.

Such "combined product" may be a compound drug containing the antitumor agent of the present invention and the existing chemotherapeutic agent as active ingredients. In addition, a single package (a formulation kit) containing the antitumor agent of the present invention and the existing chemotherapeutic agent appropriate for combined administration can be produced/packaged/distributed.

The term "combined administration" can be referred to not only simultaneous administration of the antitumor agent of the present invention and the existing chemotherapeutic agent but also administration of the antitumor agent of the present invention and the existing chemotherapeutic agent at certain intervals.

The administration dose and the administration frequency of the antitumor agent of the present invention can vary depending on factors such as patient age and weight, and severity of disease. However, the antitumor agent of the present invention can be administered at a single dose appropriately within the range of 0.0001 mg to 100 mg in terms of shRNA per kg body weight 1 to 3 times every day or every 1 to 21 days. The PEG-modified cationic liposome containing shRNA contained in the antitumor agent of the present invention has greater ability to circulate in vivo than a conventionally known complex (lipoplex) comprising an RNAi molecule and a liposome. Therefore, it is possible to avoid frequent administration. Such administration allows avoidance of in vivo foreign body detection by the immune system.

The administration dose and the administration frequency of the existing chemotherapeutic agent can vary depending on factors such as types of chemical substances contained as active ingredients, patient age and weight, and severity of disease. However, the existing chemotherapeutic agent can be administered at a single dose appropriately within the range of 0.0001 mg to 1000 mg per kg body weight 1 to 3 times every day or every 1 to 14 days. For instance, if the existing chemotherapeutic agent is a 5-FU antitumor agent, it can be administered at a daily dose of 60 to 160 mg in terms of tegafur every day or every 1 to 7 days. The existing chemotherapeutic agent can be administered at lower doses and frequencies when used in combination with the antitumor agent of the present invention compared with a case in which it is administered alone. This can suppress or delay the development of side effects that can be caused by administration of the existing chemotherapeutic agents. Examples of side effects include, but are not limited to, bone-marrow suppression, hemolytic anemia, disseminated intravascular coagulation syndrome, fulminant hepatic failure, dehydration, enteritis, interstitial pneumonia, stomatitis, gastrointestinal tract ulcer, gastrointestinal tract hemorrhage, perforation of the gastrointestinal tract, acute renal failure, muco-cutaneo-ocular syndrome, toxic epidermal necrolysis, psychoneurotic disorder, acute pancreatitis, rhabdomyolysis, and anosmia.

The present invention also relates to a method for treating cancer using the antitumor agent of the present invention. Examples of cancers treatable by the method include the cancers defined above. In addition, according to the method, the administration routes and the dosages of the antitumor agent of the present invention and the existing chemotherapeutic agents are as described above.

EXAMPLES

Hereafter, the present invention is described in greater detail with reference to the examples below. However, the present invention is not limited to these examples.

Example 1

RNAi Molecule Preparation siRNA and shRNA described below were synthesized by a conventionally known method.
(I) siRNA Targeting TS
siRNA targeting TS used herein is synthesized as the siRNA targeting TS that has been confirmed to have the antitumor effects (WO2010/113844). It comprises the sense strand and the antisense strand shown below.

Sense strand:
5'-GUAACACCAUCGAUCAUGA-3'          (SEQ ID NO: 1)

Antisense strand:
5'-UCAUGAUCGAUGGUGUUAC-3'          (SEQ ID NO: 2)

In addition, siRNA targeting TS is hereafter referred to as "siTS."
(II) siRNA Targeting Luciferase
siRNA targeting luciferase was synthesized as control siRNA. The siRNA comprises the sense strand and the antisense strand shown below.

Sense strand:
5'-CUUACGCUGAGUACUUCGATT-3'        (SEQ ID NO: 9)

Antisense strand:
5'-UCGAAGUACUCAGCGUAAGTT-3'        (SEQ ID NO: 10)

In addition, siRNA targeting luciferase is hereafter referred to as "siCont."
(III) shRNA Targeting TS
shRNA targeting TS used herein is synthesized as the shRNA targeting TS that has been confirmed to have the antitumor effects (WO2010/113844) It comprises the following sequence.

TS-shRNA:
                                   (SEQ ID NO: 8)
5'-GUAACACCAUCGAUCAUGAUAGUGCUCCUGGUUGUCAUGAUCGAUG

GUGUUAC<u>UU</u>-3'

This shRNA differs from the aforementioned conventional shRNA targeting TS in that it has the underlined two uracils (constituting an overhang). In addition, shRNA targeting TS is hereafter referred to as "shTS."

Example 2 siRNA and shRNA-Induced TS Expression Inhibition

Transfection
Lipofectamine™ RNAi MAX (hereafter referred to as "Lf RNAi MAX"), which is a cationic liposome, was used as a transfection reagent.

shRNA or siRNA prepared in Example 1 and Lf RNAi MAX were separately diluted with OptiMEM. The resulting solutions were mixed at a ratio of shRNA or siRNA to Lf RNAi MAX of 100 (pmol): 5 (μL). Here, equivalent amounts of the shRNA or siRNA solution and the Lf RNAi MAX solution were used. The obtained liquid mixture was left at room temperature for 10 to 20 minutes, resulting in complex (lipoplex) formation.

Each lipoplex was directly added to a 10-cm dish containing OptiMEM to adjust the total volume to 5 ml. Next, DLD-1 or DLD-1/FU cell suspension (10 ml) was seeded on the dish (500,000 cells/dish) so as to result in a final total volume of 15 ml, followed by transfection. Here, the final concentration of shRNA or siRNA was adjusted to 1, 5, or 10 nM. After the initiation of transfection, culture was carried out in a medium at 37° C. under 5% $CO_2$ for 72 hours. Then, the cell extract was prepared by the method described below.

Cell Extract Preparation

Seventy two (72) hours after the initiation of transfection, the medium was removed, followed by washing with cool PBS(−). Cells were detached from the dish using a trypsin solution and the supernatant was removed by centrifugation. Further, washing with cool PBS(−) was carried out. Cool Lysis buffer (50 mM Tris-HCl (pH 7.4), 1% NP-40, 0.25% sodium deoxycholate, 150 mM NaCl, and Protease Inhibitor Cocktail (Sigma-Aldrich, MO, USA)) (100 to 150 μL) was added thereto, followed by incubation on ice (4° C.) for 1 hour. Thus, the cells were lysed. Subsequently, centrifugation was performed (15,000×g, 15 minutes, 4° C.). The obtained supernatant was used as a cell extract.

SDS-PAGE Sample Preparation

Equivalent amounts of the above cell extract and a 2× sample buffer were mixed and heated using a microtube hot plate at 95° C. for 3 minutes. Subsequently, centrifugation was performed for 30 seconds, followed by cooling to room temperature. Thus, an SDS-PAGE sample was obtained.

SDS-PAGE

The sample (6 μl corresponding to 9 μg of protein/lane) was applied to gel. Such gel was connected to a power supply (Bio-Rad laboratories), and electrophoresis was performed for approximately 80 minutes at a constant current of 40 mA for two gel sheets (20 mA for a single gel sheet).

Western Blotting

Filter paper cut in pieces with adequate sizes and Hybond-ECL were immersed in blotting buffer for pretreatment. After SDS-PAGE, a transfer apparatus was used for transferring protein to Hybond-ECL. Hybond-ECL subjected to transfer was immersed in blocking buffer (5% skim milk) for blocking at room temperature for 1 hour and washed 3 times (5 minutes each) with Tween buffer.

For detection of TS and β-actin, overnight reaction was carried out at 4° C. using the following primary antibodies each diluted with Tween buffer: a mouse monoclonal anti-human TS antibody (1:1000) (ANASPEC, Inc., CA, USA); and a mouse monoclonal anti-human β-actin antibody (1:500) (Bio Vision, Inc., CA, USA). Washing with Tween buffer was conducted 3 times (5 minutes each). Then, reaction was carried out at room temperature for 1 hour using a secondary antibody (an HRP-conjugated goat anti-mouse secondary antibody (1:2000) (MP Biomedicals, LLC, Japan)) solution diluted with Tween buffer. Washing with Tween buffer was conducted 3 times (5 minutes each), followed by a reaction with an ECL chemiluminescence reagent for approximately 1 minute. The band of each protein of interest was detected on X-ray film.

FIG. 1 shows the results.

It was revealed that shRNA and siRNA prepared in Example 1 can significantly inhibit TS expression in DLD-1 cells and DLD-1/FU cells.

Example 3

Cancer Cell (Human Colorectal Cancer Cell) Proliferation Inhibitory Effects of siRNA and shRNA In this Example, experimentation was performed on a 96-well plate scale. A lipoplex obtained as in the case of Example 2 was directly added to wells containing OptiMEM to adjust the total volume to 50 μl per well. Next, a DLD-1 or DLD-1/FU cell (human colonic intestinal adenocarcinoma cell) suspension (2,000 cells/100 μl) was added to the wells to which the lipoplex had been added (final total volume: 150 μl), followed by transfection. Here, the final concentration of shRNA or siRNA per well was 5 nM.

The medium was removed from each well 24 hours after the initiation of transfection. A fresh medium containing or not containing an existing chemotherapeutic agent, 5-FU, was added thereto (200 μl per well). Here, 5-FU was added to DLD-1 so as to result in a concentration of 0.1 μg/mL. 5-FU was added to DLD-1/FU so as to result in a concentration of 10 μg/mL. The medium was removed 0, 24, 48, 72, or 96 hours after the addition of the fresh medium. A 0.5% MTT (3-(4,5-dimethylthiazole-2-yl)-2,5-diphenyltetrazolium bromide) solution was added thereto (50 μl per well), followed by incubation at 37° C. under 5% $CO_2$ for 4 hours. Also, the 0.5% MTT solution was added to cell-free wells to obtain a background absorbance.

After the completion of incubation, acidic isopropanol (150 μl) was added to each well. Formazan crystals were dissolved using a shaker. Absorbance was determined at a wavelength of 570 nm using a plate reader. Then, the cell proliferation rate was calculated.

Cell proliferation rate(%)=[$A570$($X$ hours after the addition of fresh medium)/$A570$(0 hours after the addition of fresh medium)]×100

Figure 3:
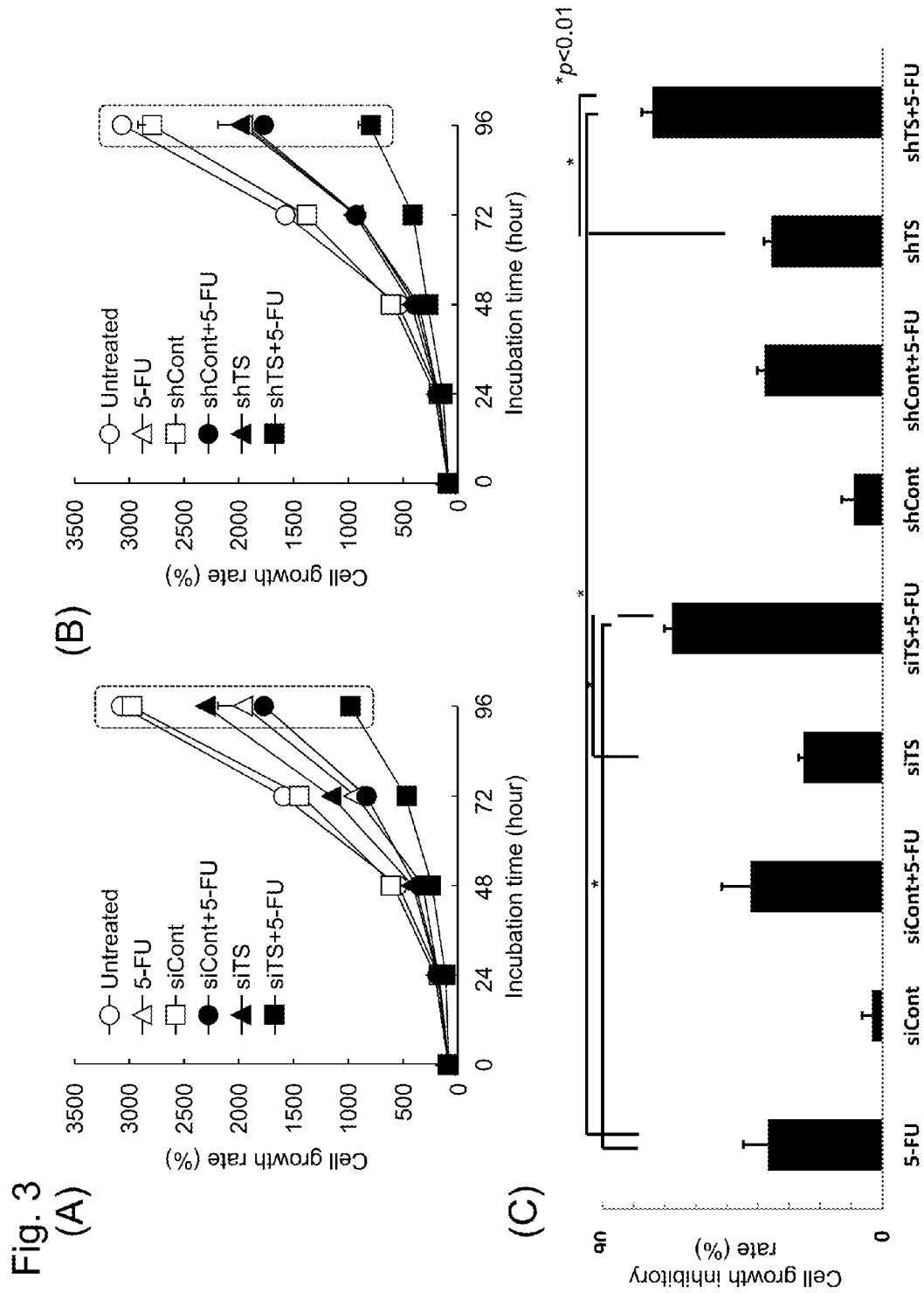
FIG. 3 (C) shows the cell growth inhibitory rate (%) for each sample 96 hours after the addition of fresh medium.

FIGS. 2 and 3 show the results.

As shown in FIGS. 2 and 3, siTS and shTS were found to have significantly inhibited proliferation of DLD-1 cells and DLD-1/FU cells in the presence of 5-FU.

Example 4

PEG-Modified Cationic Liposome Preparation

Cationic liposome was prepared using the Bangham method.

Cationic lipids (i.e., DOPE, POPC, CHOL, and DC-6-14) were separately dissolved in chloroform to prepare stock solutions. A sample was collected from each stock solution by precise measurement with the use of a glass syringe so as to result in the following lipid composition: DOPE:POPC:CHOL:DC-6-14=3:2:3:2 (molar ratio). The samples were introduced into a plugged test tube and mixed therein (the total lipid amount: 150 mmol). Next, chloroform was removed therefrom under reduced pressure using a rotary evaporator (IWAKI, Tokyo). Subsequently, the test tube was placed overnight in a vacuum pump for complete removal of chloroform. Accordingly, a lipid thin film was formed in the test tube. A 9% sucrose solution (30 mL, pH 7.4) was added as an internal water phase to the lipid thin film, followed by intensive agitation at 37° C. Thus, the lipid thin film was completely hydrolized such that MLVs (multilamellar vesicles) were formed (final lipid concentration: 50 mM). The obtained solution was heated to 37° C., during which LUVs (large unilamellar vesicles) having particle sizes of approximately 100 nm were prepared using 200-, 100-, and 50-nm polycarbonate membranes (Nucleopore, CA, USA) by an extrusion method. The particle sizes and zeta potentials of the liposomes were determined using an NICOMP 370 (Particle Sizing System, CA, USA) (with a dynamic light scattering method and an electrophoresis light scattering method, respectively). The average particle size was found to be 119.9 nm and the zeta potential was found to be 25.56 mV for the prepared liposomes.

The liposomes were PEGylated by a post insertion method. The liposome solution was prepared. Then, a 9% sucrose solution in which mPEG$_{2000}$-DSPE had been completely dissolved was added to the liposome solution such that the molar percentage of mPEG$_{2000}$-DSPE accounted for 5% of the total amount of lipids (DOPE, POPC, CHOL, and DC-6-14), followed by mild shaking in an incubator provided with a shaker at 37° C. for 1 hour.

Example 5

PEG-Modified Lipoplex Preparation

A PEG-modified lipoplex was obtained by mixing the PEG-modified cationic liposome solution prepared in Example 4 and shTS prepared in Example 1 at a ratio of cationic liposome:shTS=2000:1 (molar ratio), followed by intensive agitation for 10 minutes. The average particle size and zeta potential for the prepared PEG-modified lipoplex were found to be 286.8 nm and 15.81 mV, respectively.

Example 6

Antitumor Effects of PEG-Modified Lipoplex Upon Systemic Administration to DLD-1 Cancer-Bearing Mouse DLD-1 Cancer-Bearing Mouse Production
BALB/c nu/nu male mice were subcutaneously inoculated with a DLD-1 cell suspension ($2 \times 10^6$ cells/100 μL). On Day 8 from tumor cell inoculation, mice with tumor volumes of 50-100 mm$^3$ were subjected to an in vivo experiment.
Carcinostatic Activity Evaluation of PEG-Modified Lipoplex
The PEG-modified lipoplex was administered via the mouse caudal vein to the DLD-1 tumor-bearing mice at a dose of 80 μg/300 μL (in terms of the shRNA amount) at 1-day intervals for 8 times in total starting on day 8 after tumor transplantation.

When the existing chemotherapeutic agent ("TS-1;" Taiho Phamaceutical Co., Ltd.) was used in combination with the lipoplex, the agent was orally administered every day for 15 days at a dose of 6.9 mg (tegafur)/kg starting on day 8 after tumor transplantation.

Carcinostatic activity was examined based on changes in tumor volume and body weight.

The tumor volume was determined using the equation below.

Tumor volume(mm$^3$)=(long diameter of tumor)× (short diameter of tumor)$^2$×0.5

Figure 4:
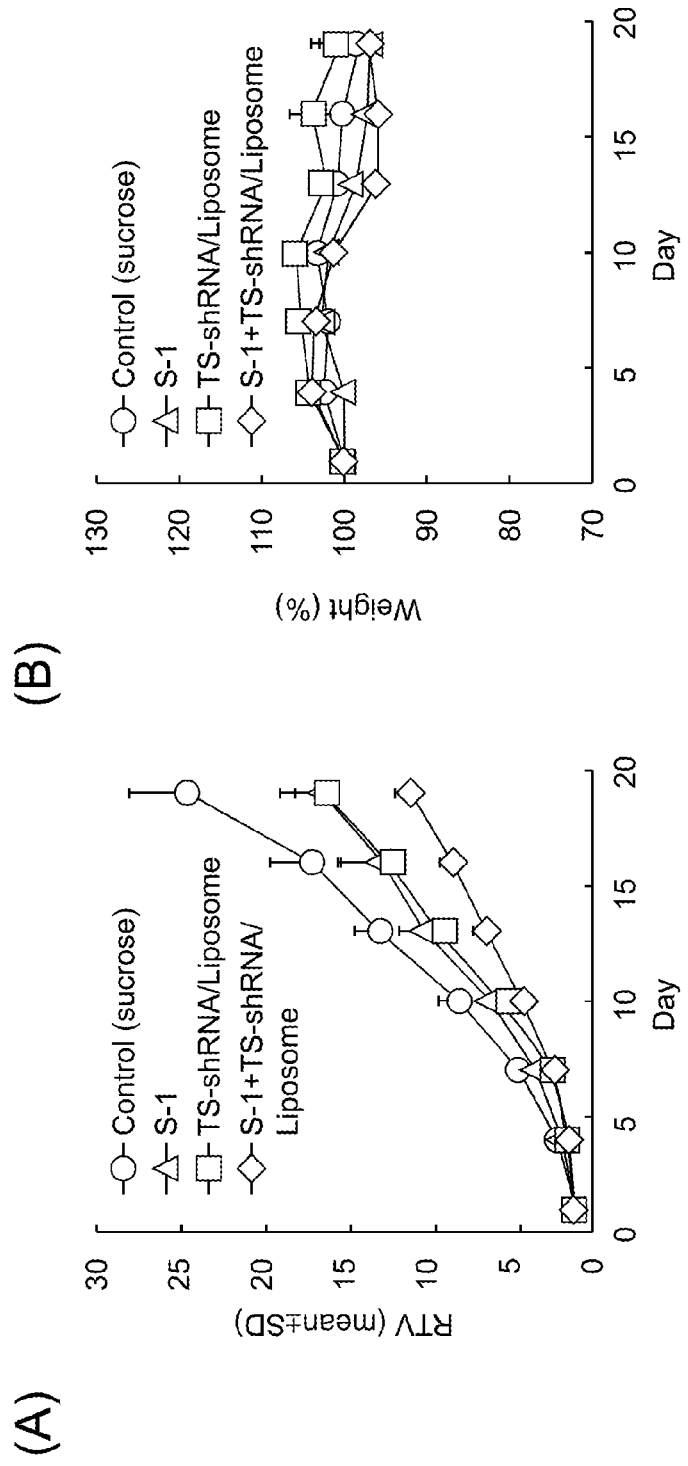
FIGS. 4(A) and 4(B) each show a characteristic chart indicating results confirmed for shRNA targeting TS under the presence or absence of S-1 in mice bearing a human colorectal cancer cell line (DLD-1) ((A): tumor growth inhibitory effects; and (B): weight increase or decrease).
Figure 5:
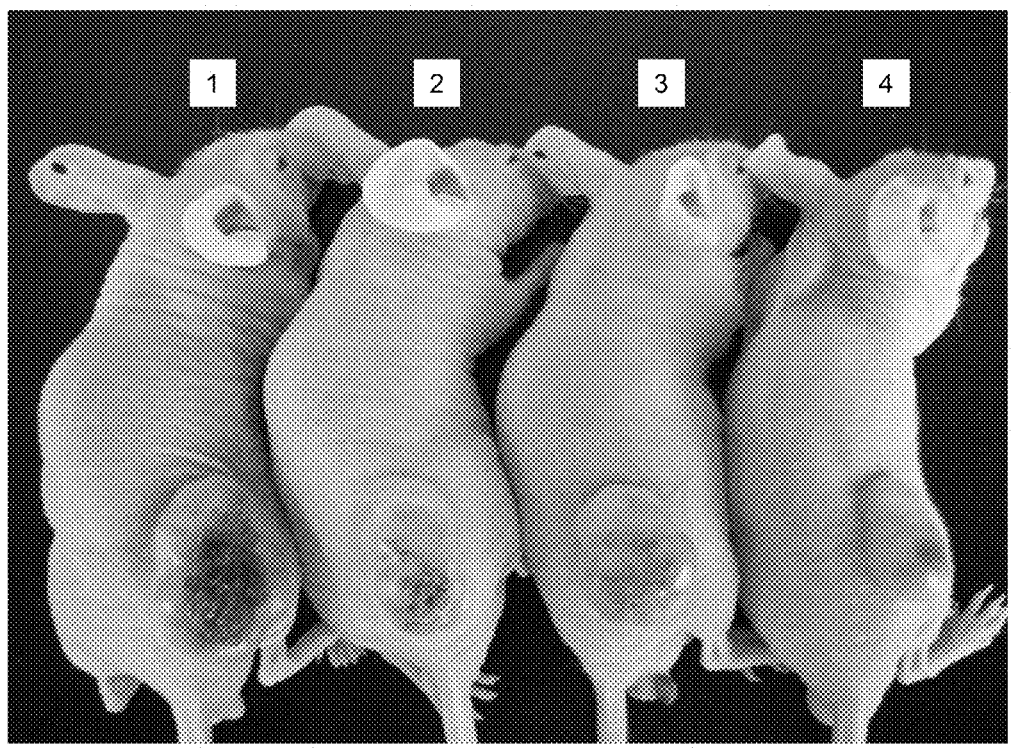
FIG. 5 shows a photo indicating tumor growth inhibitory effects confirmed for shRNA targeting TS under the presence or absence of TS-1 in mice bearing a human colorectal cancer cell line (DLD-1): 1: Control (sucrose administration); 2: S-1; 3: TS-shRNA/liposome; and 4: S-1+TS-shRNA/liposome.

FIGS. 4 and 5 show the results.
The groups treated with the use of TS-1 or the PEG-modified lipoplex preparation alone exhibited tumor growth inhibitory effects to an extent approximately 34% greater than the control group. Meanwhile, the group treated with the combination of TS-1 and the PEG-modified lipoplex preparation exhibited tumor growth inhibitory effects to an extent approximately 66% greater than the control group. Serious toxicity, which can cause weight increase inhibition, and the like, was not confirmed for any treatment group. In addition, as shown in FIG. 5, it was confirmed that tumor growth can be significantly inhibited with the combined use of the PEG-modified lipoplex preparation and TS-1.

Example 7

Figure 6:
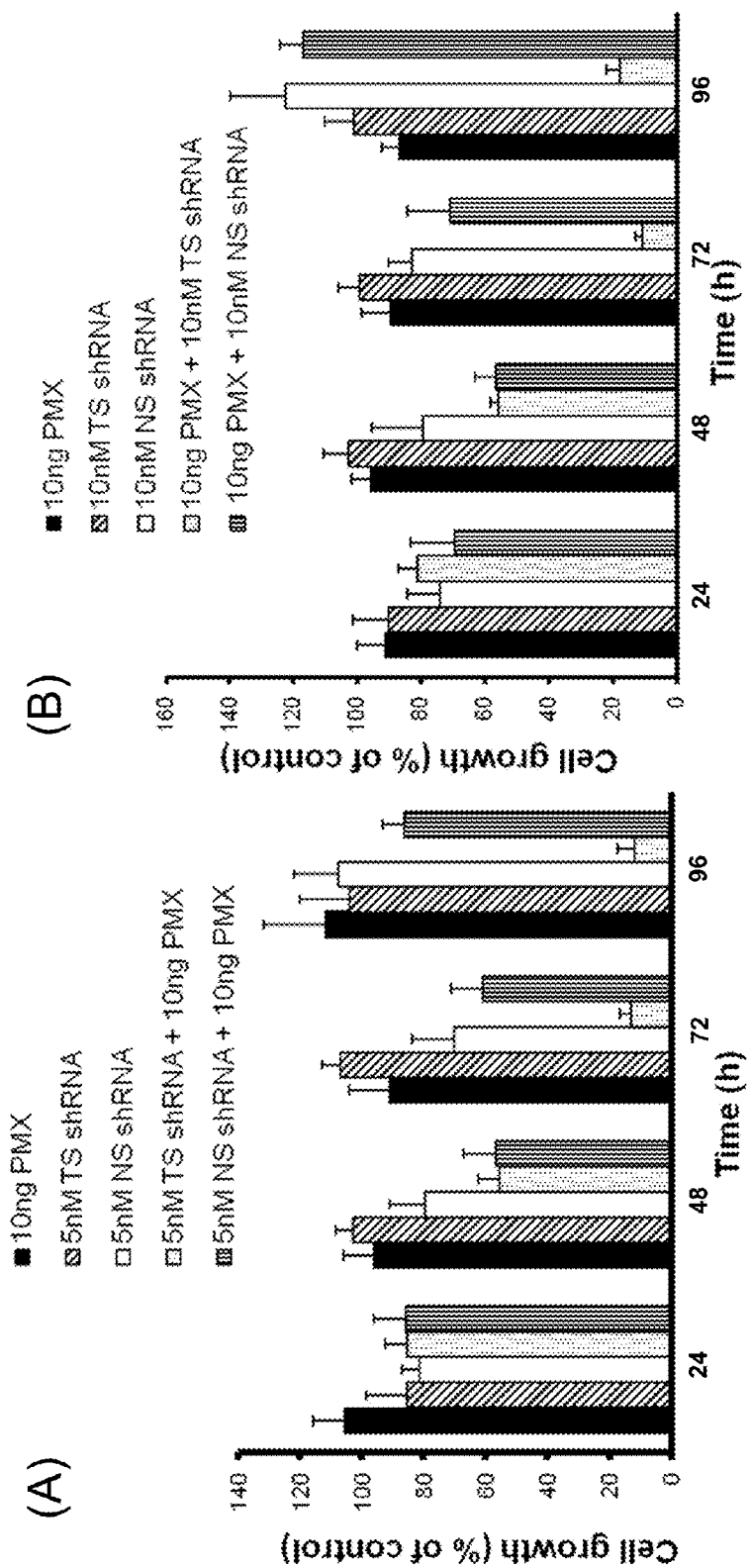
FIGS. 6 (A) and 6 (B) each show a time-dependent change of cell growth inhibitory rate (%) provided by pemetrexed sodium hydrate, shRNA targeting TS, or a combination of pemetrexed sodium hydrate and shRNA targeting TS in human plura malignant mesothelioma cell line METO 211 H.

Cancer Cell (Human Plura Malignant Mesothelioma Cell) Proliferation Inhibitory Effects of shRNA The experiment was carried out according to the method described in Example 3, except for using human plura malignant mesothelioma cell line (MSTO 211H) instead of human colorectal carcinoma cell line (DLD-1 or DLD-1/FU) and using pemetrexed sodium hydrate (Alimta (registered trademark) (Eli Lilly Japan K.K.)) instead of 5-FU as an existing chemotherapeutic agent. In the transfection, the final concentration of shRNA per well was either 5 or 10 nM. Pemetrexed sodium hydrate was added to a fresh medium at 10 ng/mL Cell proliferation rate (%) was calculated in the same manner as described in the Example 3. FIG. 6 show the results.

As shown in FIG. 6, shTS significantly inhibited proliferation of MSTO 211H cells in the presence of pemetrexed sodium hydrate.

Example 8

Antitumor Effects of PEG-Modified Lipoplex Upon Systemic Administration to MSTO 211H Cancer-Bearing Mouse MSTO 211H Cancer-Bearing Mouse Production
BALB/c nu/nu male mice were subcutaneously inoculated with a MSTO 211H cell suspension ($5 \times 10^6$ cells/100 μL). On day 14 from tumor cell inoculation, mice with tumor volumes of 50-100 mm$^3$ were subjected to an in vivo experiment.
Carcinostatic Activity Evaluation of PEG-Modified Lipoplex in MSTO 211H Cancer-Bearing Mouse
The PEG-modified lipoplex prepared in Example 5 was administered via the mouse caudal vein to the MSTO 211H tumor bearing mice at a dose of 40 μg/200 μL (in terms of the shRNA amount) at 1-day intervals for 6 times in total starting on day 14 after tumor transplantation.

When the existing chemotherapeutic agent, pemetrexed sodium hydrate (Alimta (registered trademark) (Eli Lilly Japan K.K.)), was used in combination with the lipoplex, the agent was intraperitoneally administered 6 times in total (day 1, 2, 3, 8, 9 and 10) with 100 mg/kg starting on day 14 after tumor transplantation.

Carcinostatic activity was determined with tumor growth inhibition rate (TGI) (%) at day 21 from beginning of the administration. The TGI (%) was calculated in the same manner as described in the Example 6.

Figure 7:
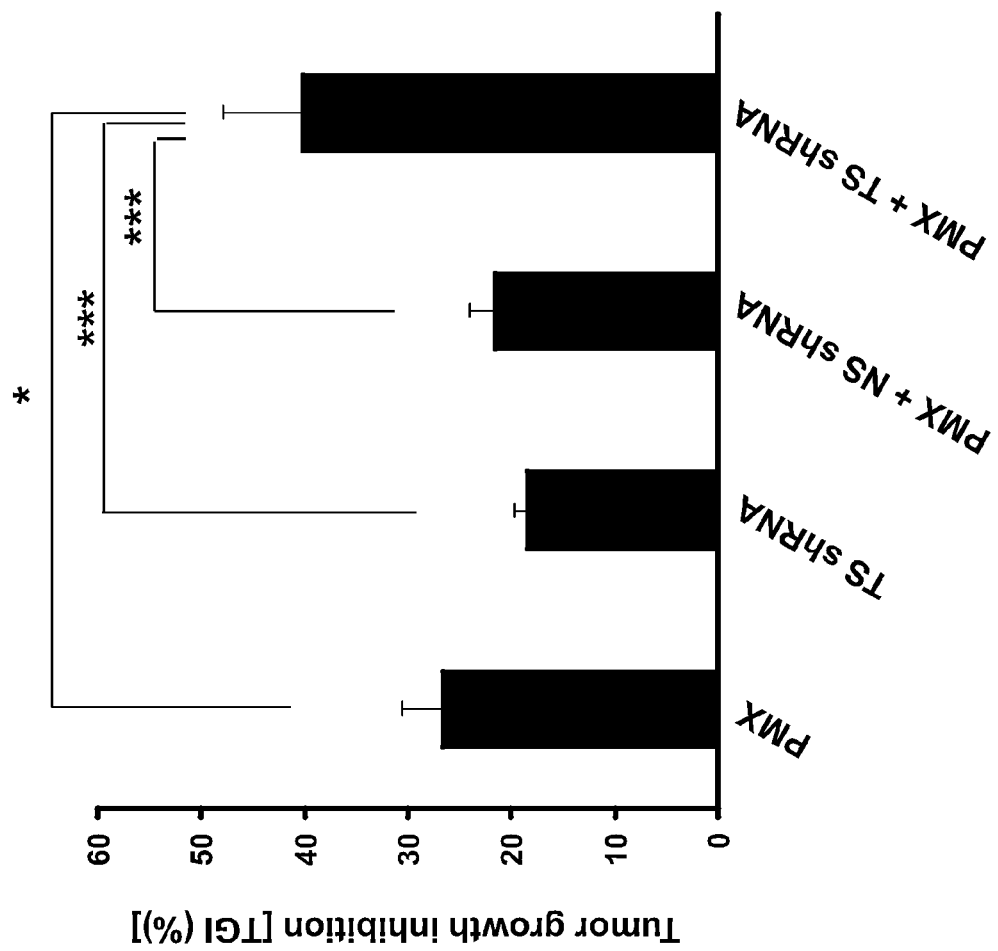
FIG. 7 shows a characteristic chart indicating tumor growth inhibitory effects confirmed for shRNA targeting TS under the presence or absence of pemetrexed sodium hydrate in mice bearing a human plura malignant mesothelioma cell line METO 211 H.

FIG. 7 shows the result.
The group treated with the pemetrexed sodium hydrate alone or the group treated with the PEG-modified lipoplex preparation containing shRNA targeting TS (TS shRNA) alone exhibited tumor growth inhibitory effects to an extent approximately 28% and 19%, respectively. The group treated with the combination of pemetrexed sodium hydrate and the PEG-modified lipoplex preparation containing non-targeted shRNA (NS shRNA) exhibited tumor growth inhibitory effects to an extent approximately 22%. This inhibitory effect by the combination of PMX and NS shRNA was similar to that of PMX alone. Meanwhile, the group treated with the combination of pemetrexed sodium hydrate and the PEG-modified lipoplex preparation containing shRNA targeting TS (TS shRNA) exhibited tumor growth inhibitory effects to an extent approximately 42%.

As shown in FIG. 7, it was confirmed that tumor growth can be significantly inhibited with the combined use of the PEG-modified lipoplex preparation containing TS-shRNA and pemetrexed sodium hydrate.

Proliferation of TS-expressing tumor can be inhibited via in vivo administration of the antitumor agent containing, as an active ingredient, a liposome containing a shRNA molecule targeting a thymidylate synthase of the present invention. Further, if the antitumor agent is used in combination with a chemotherapeutic agent, cancer tissue targetability is promoted and thus the antitumor effects can be remarkably improved. It is expected that the present invention will contribute to the field of cancer therapy.

All publications, patents, and patent applications cited herein are incorporated herein by reference in their entirety.

What is claimed is:

1. An antitumor agent, which comprises:
   short hairpin RNA (shRNA) capable of inhibiting expression of thymidylate synthase by RNAi action; and
   a PEG-modified cationic liposome,
   wherein the shRNA is bound to the surface of the PEG-modified cationic liposome and has an overhang comprising at least two nucleotides at the 3' end and the PEG-modified cationic liposome comprises a catonic liposome composed of dioleoylphosphatidylethanolamine (DOPE), palmitoyloleoylglycerophosphocholine (POPC), cholesterol (CHOL), and O,O'-ditetradecanoyl-N-(α-trimethylammonioacetyl)diethanolaminechloride (DC-6-14) at a molar ratio of 3:2:3:2.

2. The antitumor agent according to claim 1, wherein the shRNA comprises a sense strand consisting of the nucleotide sequence shown in SEQ ID No: 1 and an antisense strand that hybridizes under stringent conditions to the sense strand.

3. The antitumor agent according to claim 1, wherein the shRNA comprises a sense strand consisting of the nucleotide sequence shown in SEQ ID No: 1 and an antisense strand consisting of the nucleotide sequence shown in SEQ ID NO: 2.

4. The antitumor agent according to claim 1, wherein the shRNA consists of the nucleotide sequence shown in SEQ ID No: 8.

5. The antitumor agent according to claim 1, wherein the particle size of the antitumor agent is 200 to 300 nm.

6. The antitumor agent according to claim 1, wherein further siRNA or shRNA capable of inhibiting expression of a gene selected from the group consisting of genes involved in tumor cell proliferation is bound to the surface of the PEG-modified cationic liposome.

7. The antitumor agent according to claim 6, wherein the gene involved in tumor cell proliferation is at least one gene selected from the group consisting of genes encoding VEGF, EGFR, PDGF, HGF, Wint, Bcl-2, survivin, ribonucleotide reductase, and DNA polymerase.

8. A combined product, which contains the antitumor agent according to claim 1 and a chemotherapeutic agent for treating tumors.

9. The combined product according to claim 8, wherein the chemotherapeutic agent for treating tumors is an antitumor agent having TS inhibitory action.

10. The antitumor agent or the combined product according to claim 9, wherein the antitumor agent having TS inhibitory action is a 5-FU antitumor agent or pemetrexed sodium hydrate.

11. The antitumor agent or the combined product according to claim 10, wherein the 5-FU antitumor agent is a compound drug of tegafur, gimeracil, and oteracil potassium.

12. A method for treating cancer, which comprises administering the antitumor agent according to claim 1 to a cancer patient.

13. The method according to claim 12, which further comprises administrating a chemotherapeutic agent for treating tumors in combination with the antitumor agent.

14. The method to claim 13, wherein the chemotherapeutic agent for treating tumors is an antitumor agent having TS inhibitory action.

15. The method according to claim 14, wherein the antitumor agent having TS inhibitory action is a 5-FU antitumor agent or pemetrexed sodium hydrate.

16. The method according to claim 15, wherein the 5-FU antitumor agent is a compound drug of tegafur, gimeracil, and oteracil potassium.

17. The method according to claim 12, wherein the cancer is selected from the group consisting of colorectal cancer, liver cancer, kidney cancer, head and neck cancer, esophageal cancer, gastric cancer, biliary tract cancer, gallbladder and bile duct cancer, pancreatic cancer, lung cancer, mammary cancer, ovarian cancer, cervical cancer, uterine body cancer, bladder cancer, prostate cancer, testicular tumor, osteogenic and soft-tissue sarcomas, leukaemia, malignant lymphoma, multiple myeloma, skin cancer, brain tumor and plura malignant mesothelioma.

* * * * *